United States Patent
Hatton et al.

(10) Patent No.: US 9,068,198 B2
(45) Date of Patent: *Jun. 30, 2015

(54) CHINESE HAMSTER OVARY CELL LINE

(75) Inventors: Diane Hatton, Cambridge (GB); Ray Field, Cambridge (GB); Wyn Forrest-Owen, Cambridge (GB); Victoria Richardson, Finedon Northamptonshire (GB)

(73) Assignee: MedImmune Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/822,371

(22) PCT Filed: Sep. 14, 2011

(86) PCT No.: PCT/EP2011/065966
§ 371 (c)(1),
(2), (4) Date: May 15, 2013

(87) PCT Pub. No.: WO2012/035079
PCT Pub. Date: Mar. 22, 2012

(65) Prior Publication Data
US 2014/0011237 A1 Jan. 9, 2014

Related U.S. Application Data

(60) Provisional application No. 61/383,005, filed on Sep. 15, 2010.

(51) Int. Cl.
C12N 15/85 (2006.01)
C12P 21/00 (2006.01)
C12N 5/071 (2010.01)

(52) U.S. Cl.
CPC ............. *C12N 15/85* (2013.01); *C12N 2510/02* (2013.01); *C12N 2511/00* (2013.01); *C12P 21/00* (2013.01); *C12N 5/0682* (2013.01)

(58) Field of Classification Search
CPC ............... C12N 15/85; C12N 2510/02; C12N 2511/00; C12N 5/0681; C12N 2670/18522; C12N 2800/22; C12N 2830/48; C12P 21/00; C07K 14/005; C07K 2319/21
See application file for complete search history.

(56) References Cited

FOREIGN PATENT DOCUMENTS

WO   WO 2009/046978 A1    4/2009
WO   WO 2011/033005    *   4/2011   ............... C12N 5/00

OTHER PUBLICATIONS

Leskowwitz et al., Adenovirus-Based Vaccines against *Rhesus Lymphocryptovirus* EBNA-1 Induce Expansion of Specific CD8+and CD4+T Cells in Persistently Infected Rhesus Macaques., Journal of Virology, 2014, vol. 88, pp. 4721-4735.*
Edmonds, M. Celina de la Cruz et al., 2006, "Development of Transfection and High-Producer Screening Protocols for the CHOK1SV Cell System", Molecular Biotechnology, 34:179-190.
International Search Report corresponding to PCT/EP2011/065966 dated Jan. 20, 2012.

(Continued)

Primary Examiner — Alexander Kim

(57) ABSTRACT

The present invention is related to a Chinese hamster ovary cell line as deposited with the European Collection of Cell Cultures (ECACC) under accession number 10090201; use of the cell line for the production of a recombinant polypeptide; a kit comprising the cell line; and methods for the production of recombinant polypeptide.

6 Claims, 4 Drawing Sheets

(56) References Cited

OTHER PUBLICATIONS

Jiang, Zhou, 2006, "Regulation of Recombinant Monoclonal Antibody Production in Chinese Hamster Ovary Cells: A Comparative Study of Gene Copy Number, mRNA Level, and Protein Expression", Biotechnology Progress, 22:313-318.

O'Callaghan, Peter M. et al., 2010, Cell Line-Specific Control of Recombinant Monoclonal Antibody Production by CHO Cells, Biotechnology and Bioengineering, 106(6):938-951.

Schlatter, Stefan et al., 2005, "On the Optimal Ratio of Heavy to Light Chain Genes for Efficient Recombinant Antibody Production by CHO Cells", Biotechnology Progress, 21(1):122-133.

Wurm, Florian M., 2004, "Production of recombinant protein therapeutics in cultivated mammalian cells", Nature Biotechnology, 22(11):1393-1398.

Zang, Michael et al., 1995, "Production of Recombinant Proteins in Chinese Hamster Ovary Cells Using a Protein-Free Cell Culture Medium", Biotechology, 13:389-392.

* cited by examiner

CHINESE HAMSTER OVARY CELL LINE

CROSS REFERENCE TO RELATED APPLICATIONS

This application is a National Stage Application of International Application No. PCT/EP2011/065966 filed on Sep. 14, 2011, said International Application No. PCT/EP2011/065966 claims benefit under 35 U.S.C. §119(e) of U.S. Provisional Application No. 61/383,005 filed Sep. 15, 2010. Each of the above listed applications is incorporated by reference herein in its entirety for all purposes.

TECHNICAL FIELD

The present invention relates to a Chinese hamster ovary (CHO) cell line, and use of the CHO cell line for production of recombinant polypeptides, and a kit comprising the cell line.

BACKGROUND ART

CHO cell lines are derived from the ovary of the Chinese hamster (*Cricetulus griseus*) Tjio, J. H., and Puck T. T. (1958) *J. Exp. Med.*, 108(2), pp. 259-268). They are considered an ideal system for expressing recombinant proteins as post-translational protein modification is similar to that of human cells. Thus, they are the most widely used mammalian cells for transfection, expression, and large-scale recombinant protein production. CHO cells have a well-characterized approval history for production of clinical grade materials such as recombinant antibody therapeutics.

CHO-S is a known, commercially available (Invitrogen), suspension-adapted CHO cell line. CHO-S is used for expression of recombinant polypeptides in suspension culture and it is considered useful for protein production. However, for increased efficiency of polypeptide production, there is a desire to achieve higher protein expression levels than are achievable using currently available cell lines.

Thus, there is a need to improve the expression of polypeptides in CHO cell lines, to improve efficiency in manufacture of recombinant proteins.

It is an object of the present invention to provide an improved CHO cell line suitable to provide increased polypeptide yields from suspension cultures.

SUMMARY OF THE INVENTION

According to a first aspect of the present invention there is provided a Chinese hamster ovary cell line as deposited with the European Collection of Cell Cultures (ECACC) under accession number 10090201.

The cell line of the invention has an advantage of being capable of good expression of recombinant polypeptides in suspension culture. For example, the cell line of the invention advantageously provides an improved yield of recombinant polypeptide relative to the CHO-S cell line.

The cell line can further comprise a nucleic acid sequence encoding a recombinant polypeptide or multiple recombinant polypeptides. The cell line can comprise nucleic acid encoding at least two recombinant polypeptides. The nucleic acid encoding the recombinant polypeptide(s) can be episomal, for example, the nucleic acid encoding the recombinant polypeptide(s) can be comprised in a vector, such as a viral or plasmid vector. In an alternative embodiment, the nucleic acid encoding the recombinant polypeptide is chromosomal having been integrated into the host cell chromosome or an artificial chromosome.

The recombinant polypeptide can comprise an antibody light chain or heavy chain, or fragment of an antibody light chain or heavy chain, or a $V_H$ or $V_L$ domain, or fragment thereof. The recombinant polypeptide can be a heavy or light chain of an IgG class antibody, or a fragment thereof. The recombinant polypeptide can be selected from a therapeutic protein; prodrug; enzyme; enzyme fragment; enzyme inhibitor; enzyme activator; biologically active polypeptide; hedgehog protein; bone morphogenetic protein; growth factor; blood clotting factor; insulin; erythropoietin; thrombopoietin; G-CSF; interleukin; interferon; immunoglobulin; an immunoglobulin fragment, such as a Fab, Fv, scFv or dAb; and combinations thereof.

According to another aspect of the invention, there is provided the use of the cell line of the invention for the production of a recombinant polypeptide.

According to another aspect of the invention, there is provided a method for the production of a recombinant polypeptide comprising use of the CAT-S cell line of the invention.

According to another aspect of the invention, there is provided a kit comprising the CAT-S cell line of the invention and a vector encoding a recombinant polypeptide.

According to another aspect of the invention, there is provided a method for the production of a recombinant polypeptide comprising:
 culturing the cell line of the invention comprising nucleic acid encoding a recombinant polypeptide to express the recombinant polypeptide therefrom;
 at least partially purifying the recombinant polypeptide from the cells.

The skilled person will appreciate that features of any one embodiment or aspect of the invention may be applied, where appropriate, to other embodiments or aspects of the invention.

The following abbreviations and nomenclature are used herein:
 CHO Chinese Hamster Ovary
 CHOK1 The parent CHO cell line from which CAT-S is derived (ECACC accession 85051005)
 CHO-S Suspension adapted CHO cell line (Invitrogen)
 CAT-S The cell line of the invention deposited with the European Collection of Cell Cultures (ECACC) under accession number 10090201
 hCMV-MIE Human cytomegalovirus major intermediate early
 HPLC High Performance Liquid Chromatography
 CD-CHO Chemically defined media for CHO cells (Invitrogen)
 MSX Methionine sulfoximine
 UTR Untranslated leader sequence

Figure 1:
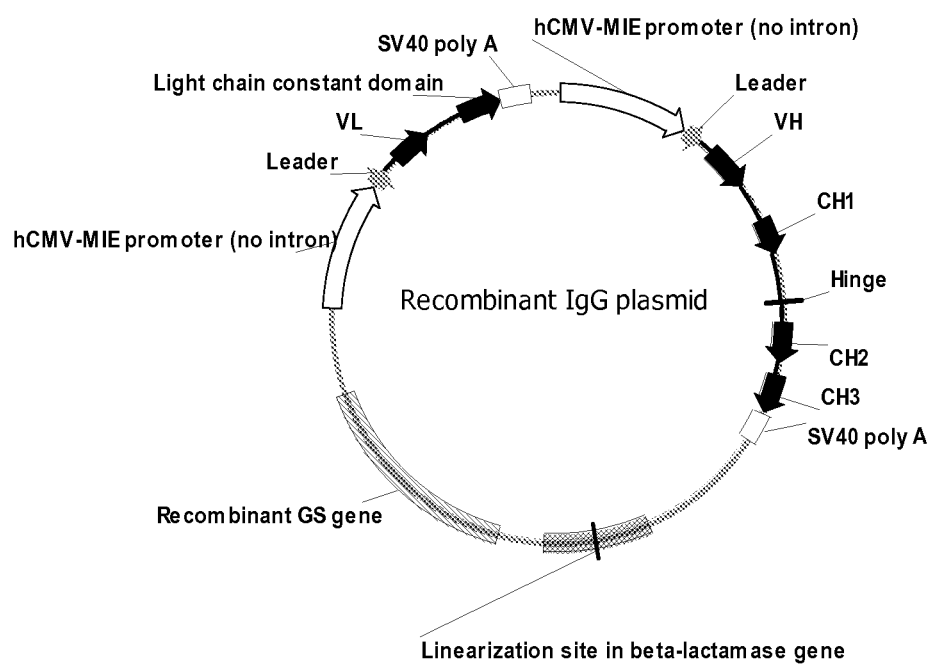
FIG. 1 shows a plasmid for selection and expression of recombinant IgG in CHO cells.

The invention will now be exemplified by the following non-limiting examples.

EXAMPLES

Biological Deposit

The CATS cell line of the invention was deposited, in accordance with The Budapest Treaty of 1977, on 2 Sep. 2010 with the European Collection of Cell Cultures (ECACC) under accession number 10090201.

ECACC has the following address:
European Collection of Cell Cultures
Health Protection Agency
Centre for Emergency Preparedness and Response
Porton Down, Salisbury, SP40JG, United Kingdom.

Generation and Evaluation of a CHO Suspension Cell Line, CAT-S, for Use as a Host for Expression of Recombinant Protein

Methods

Generation of the CAT-S Host Cell Line

CHOK1 cells were recovered from a cryopreserved vial (ECACC accession 85051005) into Ham's F12 medium (SAFC) supplemented with 10% FBS (HyClone) and 2 mM glutamine (Gibco) in a T25 cm$^2$ flask and grown in a static humidified incubator at 37° C. and 5% $CO_2$ for 3 days. Then, the cells were subcultured at an approximately 1:15 ratio with fresh medium in a T75 cm$^2$ flask, first using TrypZean (SAFC) to detach and dissociate the cells. After 6 days of static incubation, the cells were subcultured, again using TrypZean, by a 1:10 dilution in fresh medium, which contained a 50% volume of Ham's F12, 10% FBS and 2 mM L-glutamine and a 50% volume of CD-CHO (animal component free, chemically-defined medium from Invitrogen) with 2 mM L-glutamine, in a T75 cm$^2$ flask. Following a further 6 days of static incubation, the naturally detached cells in the culture supernatant were removed from the T75 cm$^2$ flask, centrifuged and then resuspended in fresh medium (15 mL total volume) containing 50% CD-CHO with 2 mM L-glutamine and 50% volume Ham's F12 with 10% FBS and 2 mM L-glutamine, then transferred to an Ehrlenmeyer flask and grown on a shaking platform (140 rpm) in a humidified incubator at 37° C. with 5% $CO_2$. After 7 days incubation, the cells in suspension were removed into a fresh flask leaving behind any large cell clumps and an additional 5 mL of CD-CHO with 2 mM L-glutamine was added to the culture. Following a further 7 days of growth, the cells reached approximately 2×10$^5$ viable cells/ml and the cells in suspension were again removed before being centrifuged and resuspended in the same volume of medium containing 50% fresh CD-CHO with 2 mM L-glutamine and 50% conditioned medium prepared by 0.2 µm filtration of the centrifuged culture supernatant. After 6 days of growth, an additional 5 ml CD-CHO with 2 mM glutamine was added to the cells before incubating for a further 3 days, when the cells in suspension were centrifuged and then resuspended in the same volume of fresh CD-CHO with 2 mM L-glutamine. After 7 days, the centrifugation and resuspension in fresh CD-CHO with 2 mM L-glutamine was repeated and then the cells were then subcultured five times to 2×10$^5$ viable cells/ml with fresh CD-CHO with 6 mM L-glutamine every 3-7 days before being cryopreserved at 1×10$^7$ viable cells/vial in CD-CHO medium containing 10% FBS and 7.5% DMSO (SAFC). This suspension-adapted cell stock was designated as the CAT-S host cell line. Prior to transfection, a vial of the CAT-S stock was revived and subcultured several times in CD-CHO with 6 mM L-glutamine.

Cell Culture of Host Cells

CAT-S suspension CHO cells and CHO-S suspension cells (Invitrogen) were maintained in CD-CHO medium supplemented with 6 mM L-glutamine. Cells were cultured in 5% $CO_2$ at 37° C. in a humidified, shaking incubator set at 140 rpm. Cell growth and viability were determined every 3-4 days by trypan blue exclusion staining and haemocytometry. Viability generally ranged from 88-99% viability for the CAT-S cell line and 97-99% for the CHO-S cell line.

Recombinant IgG expression plasmid

A recombinant IgG expression plasmid was constructed from pNEB193(New England Biolabs) into which the IgG heavy and light chain genes, including introns, were cloned along with a recombinant glutamine synthetase (GS) gene as a selectable marker in CHO cells. The heavy and light chain genes were assembled with the human CMV major intermediate early gene (hCMV-MIE) promoter to drive transcription and an SV40 sequence for transcript termination and polyadenylation. The hCMV-MIE promoter, without an intron, was derived from plasmid pCEP4 (Invitrogen), DNA sequences encoding an IgG 5' UTR and secretory leader peptide were included 5' of the heavy and light chain coding regions. The leader peptide facilitates targeting of translated heavy and light chain polypeptides for secretion from CHO cells. The recombinant GS gene was initially assembled in pSI (Promega) by cloning a cDNA sequence encoding hamster GS (isolated from hamster tissue) into the SV40 promoter and termination-polyadenylation expression cassette and then transferred into the pNEB193 plasmid. The structure of this recombinant IgG expression plasmid is shown in FIG. 1.

Stable expression of recombinant IgG

Transfections

CAT-S cells and CHO-S cells were pelleted by centrifugation and washed in fresh CD-CHO before being pelleted again and resuspended in fresh CD-CHO. Linearized plasmid DNA encoding a recombinant IgG and glutamine synthetase was then integrated into the cell genome. Suitable transfection methods include electroporation or nucleofection of 2 to 40 µg DNA using either an electroporator such as a Gene Pulser (Bio-Rad), or an Amaxa nucleofector (Lonza). Following transfection, cells were immediately resuspended in pre-warmed CD-CHO medium and distributed into 96-well plates. The plates were incubated in a humidified static incubator at 36.5° C., 5% $CO_2$ overnight and then selective medium, CD-CHO containing methionine sulfoximine (MSX; Sigma), was added to each well to give a final concentration of 50-75 µM MSX. The plates were incubated statically for 3-5 weeks to allow transfectant colonies to develop. Once colonies had appeared, wells with single colonies were identified and a 20 μL aliquot of supernatant removed from each well for protein quantification by ELISA.

Pool Transfections

CAT-S cells and CHO-S cells were pelleted by centrifugation and washed in fresh CD-CHO before being pelleted again and resuspended in fresh CD-CHO. Linearized plasmid DNA encoding a recombinant IgG and glutamine synthetase was then integrated into the cell genome. Suitable transfection methods include electroporation or nucleofection of 2 to 40 μg plasmid DNA using either an electroporator such as a Gene Pulser (Bio-Rad), or an Amaxa nucleofector (Lonza). Following transfection, cells were immediately resuspended in pre-warmed CD-CHO medium and distributed as into T25 $cm^2$ flasks and wells of a 24-well plate. The cells were incubated in a humidified static incubator at 36.5° C., 5% $CO_2$ overnight and then the next day selective medium (CD-CHO containing MSX) was added to each T25 $cm^2$ flask and each well of the 24-well plate to a final concentration of MSX of 50-75 μM. Flasks and plates were incubated statically for 2 to 3 weeks to recover transfectant cells.

Transfectant Culture Scale-Up and Assessment for Recombinant IgG Expression

Clonal transfectants

Colony supernatants from wells containing single colonies were assessed by ELISA for recombinant IgG production. Those colonies expressing detectable levels of IgG were then expanded into 1 mL CD-CHO containing selective MSX in the well of a 24-well plate and serially subcultured. Parallel 24-well plate cultures were created and allowed to overgrow for 14 days before assessing IgG titre by Protein A-HPLC. Transfectants with the highest IgG titre were expanded to 5 mL in CD-CHO containing MSX in T25 $cm^2$ flasks and a parallel T25 $cm^2$ culture set up for static batch overgrow and assessment of antibody titre by Protein A-HPLC. The cultures with the best titres were identified and expanded into 25 mL shake flask culture (in E125 $cm^3$ flasks) before final assessment of protein expression and cell growth in 50 mL shake flask fed-batch culture using CD-CHO medium and a chemically-defined feed (in E250 $cm^3$ flasks).

Pool Transfectants

Transfectant pools recovered in T25 $cm^2$ flasks were expanded to 15 mL in T75 $cm^2$ flasks and then into 25 mL in E125 $cm^3$ shake flask cultures in CD-CHO containing MSX. An aliquot of 5 mL was removed from the 25 mL shaking culture and placed into a T25 $cm^2$ flask for a 14-day static overgrow assessment of protein expression by protein A-HPLC.

Transfectant pools recovered in 24-well plates were initially subcultured in 24 well-plates. On the following subculture a duplicate plate was set up for a 14-day static 24-well plate overgrow assessment of protein expression by protein A-HPLC.

Results and Discussion

The potential of utilizing CAT-S cells as a host for production of manufacturing cell lines expressing recombinant IgG has been evaluated. CAT-S host cell line were compared with a commercially-available host CHO cell line, CHO-S (Invitrogen), by transfecting both cell hosts with the same vector construct encoding a recombinant human IgG and estimating peak levels of IgG production that can be achieved from these host cells. The construct was electroporated into CAT-S and CHO-S cells and cells were diluted for transfectant clone or pool evaluation by dispersing transfected cells across 96-well plates, T25 $cm^2$ flasks or 24-well plates. The IgG vector construct included a glutamine synthetase selectable marker gene allowing selection of transfectants in glutamine-free medium supplemented with the glutamine synthetase inhibitor, MSX.

Evaluation of Recombinant IgG Expression from Clonal Transfectants

Figure 2:
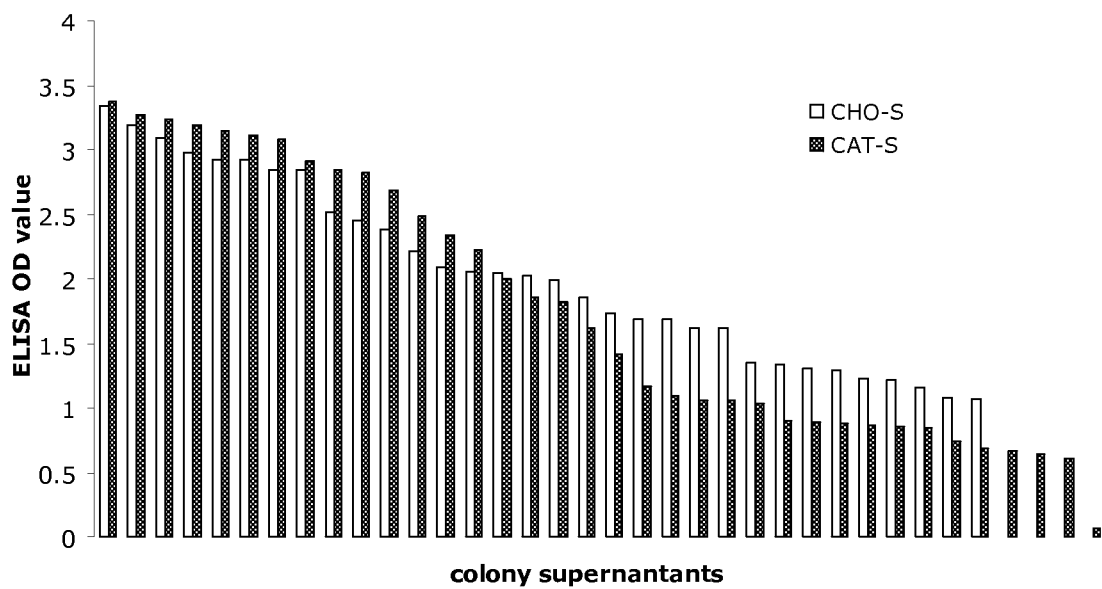
FIG. 2 shows an ELISA analysis of 96-well plate CAT-S and CHO-S colony supernatants for recombinant IgG expression.

For the clonal evaluation, supernatant from wells containing single transfectant colonies was evaluated by ELISA analysis for recombinant IgG expression (FIG. 2). Of the 36 CAT-S clones examined approximately 97% were positive by ELISA for IgG expression. Similarly, 100% of the 32 CHO-S derived colonies were positive by ELISA for IgG expression. ELISA OD profiles indicate that expression levels from transfectants from either CAT-S or CHO-S were approximately equivalent at the colony stage.

Figure 3:
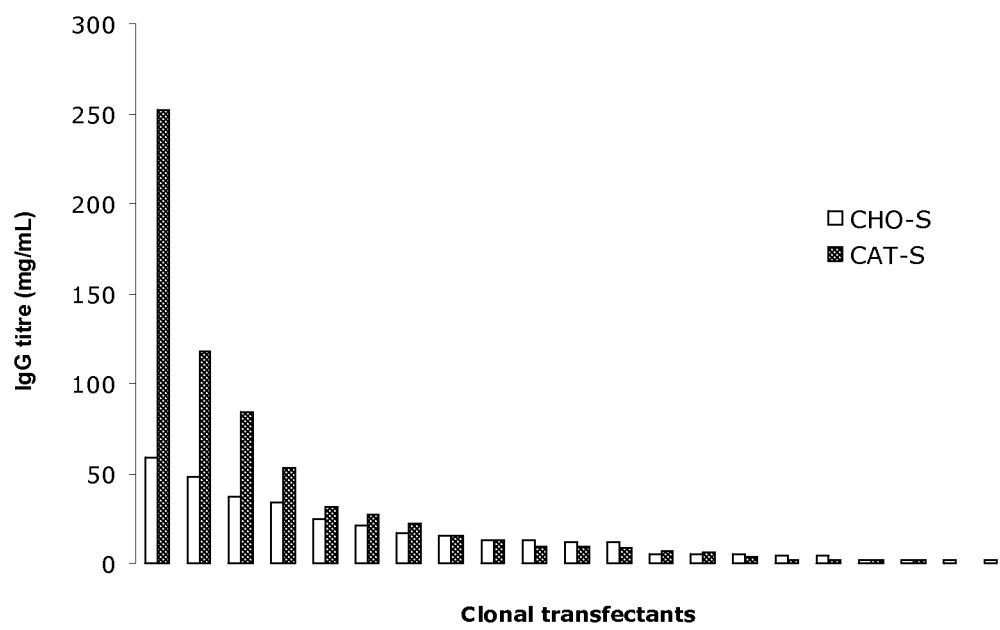
FIG. 3 shows a protein-A HPLC analysis of 24-well plate CAT-S and CHO-S 14 day transfectant supernatants for recombinant IgG expression.
Figure 4:
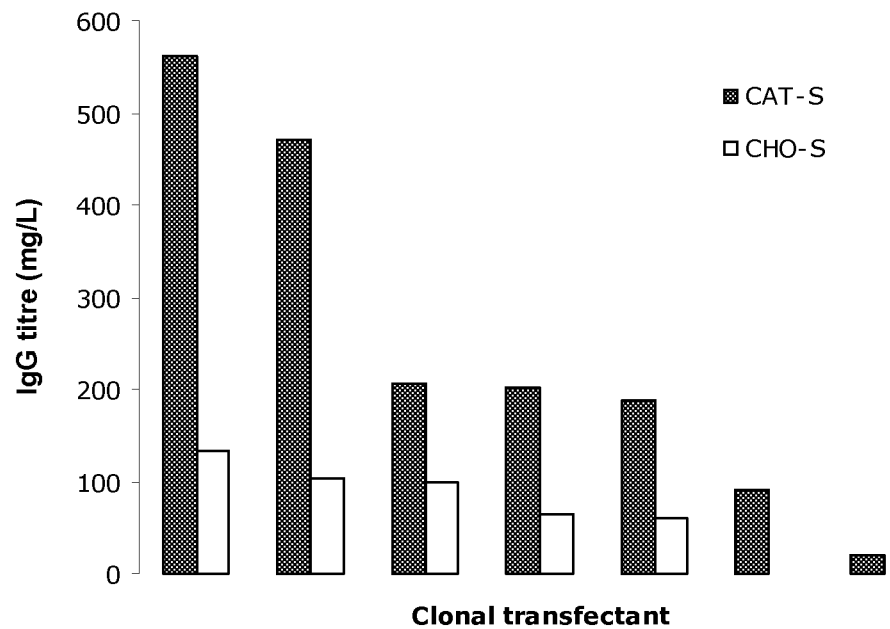
FIG. 4 shows a protein-A HPLC analysis of static T25 cm$^2$ CAT-S and CHO-S 14 day transfectant supernatants for recombinant IgG expression.
Figure 5:
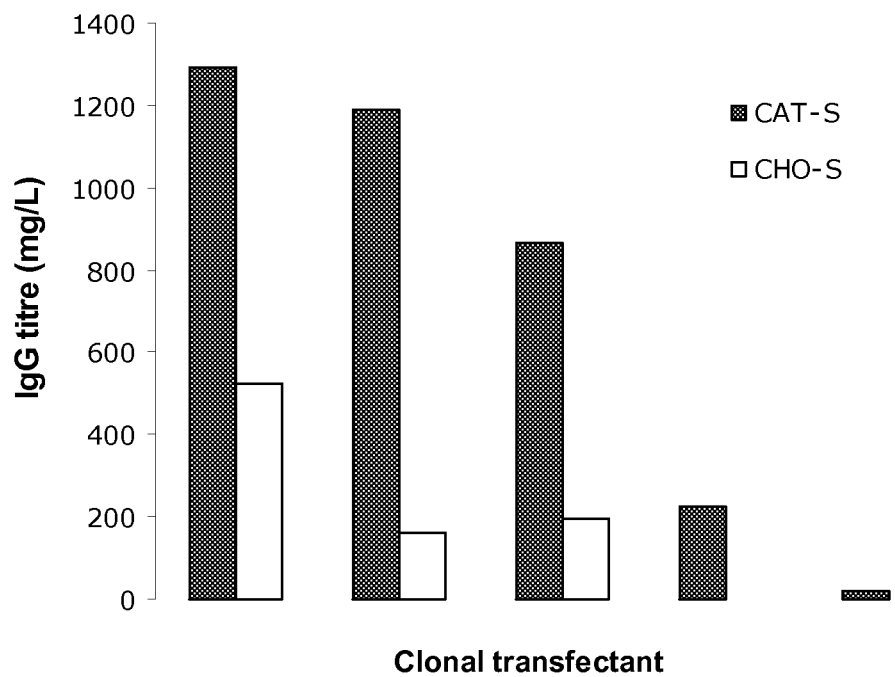
FIG. 5 shows a fed-batch shake flask overgrow analysis of CAT-S and CHO-S derived transfectants showing recombinant IgG titre at day 14 as analysed by protein-A HPLC.

Each colony identified as positive for IgG production was expanded to a well of a 24-well plate and allowed to grow for 14 days before assessing the supernatants for recombinant IgG titre by Protein-A HPLC analysis (FIG. 3). The level of recombinant human IgG was equivalent to 4-fold greater from the highest-producing CAT-S cell line compared to the highest-producing CHO-S cell line. These transfectants were ranked by titre and the highest CAT-S (7) and CHO-S (5) transfectants were chosen for further analysis by expansion in 5 mL CD-CHO with MSX in T25 $cm^2$ flasks and allowed to grow for 14 days before assessment for recombinant IgG titre by Protein-A HPLC analysis (FIG. 4). Titre data demonstrated that levels of recombinant human IgG were equivalent to 4-fold greater comparing the highest-producing CAT-S cell line to the highest-producing CHO-S cell line. Based on this data, the five CAT-S and three CHO-S transfectants expressing the highest levels of IgG were progressed into 50 mL fed-batch shake flask overgrow analysis in CD-CHO medium with chemically-defined feed (FIG. 5). Supernatant protein-A HPLC analysis showed that the harvest titres of recombinant IgG from the top three CAT-S transfectants were 2.5 to 4-fold higher than from the top three CHO-S transfectants.

Evaluation of Recombinant IgG Expression from Transfectants Pools

Figure 6:
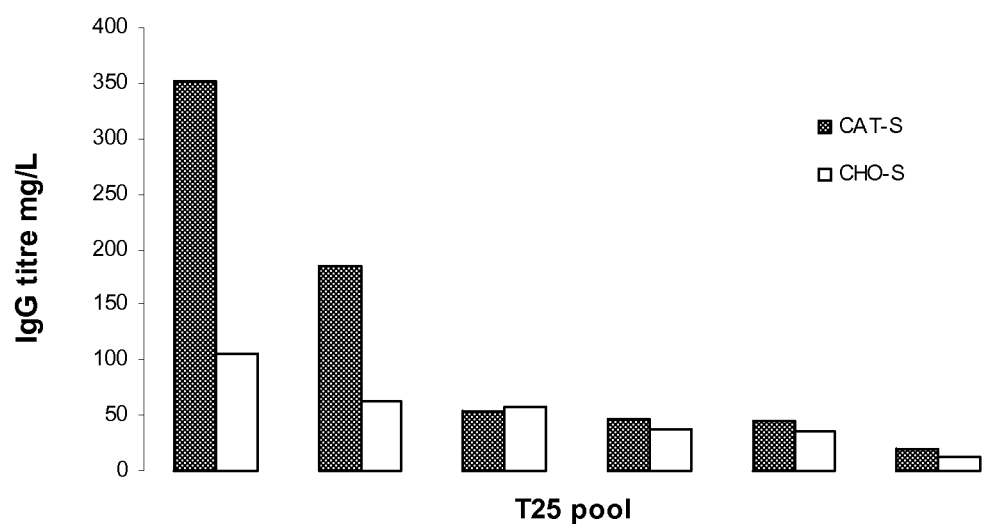
FIG. 6 shows an overgrow analysis of CAT-S and CHO-S transfectant pools showing recombinant IgG titre at day 14 as analysed by protein-A HPLC from A: T25 cm$^2$ flasks; and B: 24-well plates.
Figure 6:
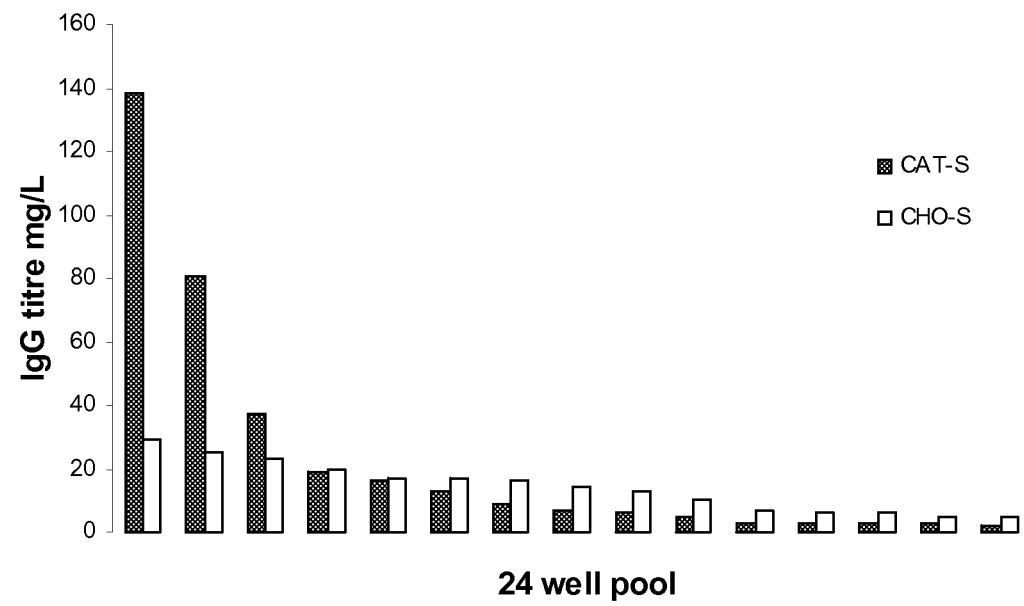

Transfectant pools of cells originating from T25 $cm^2$ flasks were expanded into shaking culture and evaluated for recombinant IgG expression by Protein-A HPLC analysis of 14-day static overgrow in T25 $cm^2$ flasks (FIG. 6a). Transfected pools of cells originating from 24-well plates were subcultured in to 24-well plates before evaluation for recombinant IgG expression by Protein-A HPLC analysis of 14-day static overgrow in 24-well plates (FIG. 6b). Analysis of day 14 harvest samples by Protein-A HPLC showed that the highest levels of recombinant IgG were achieved from CAT-S transfectant pools in both T25 $cm^2$ and 24-well plate assessments, the best being approximately 3 to 5-fold higher than the highest CHO-S pool.

CAT-S is capable of expressing recombinant IgG from stable transfection and is suitable for use in manufacturing cell line development. CHO cells are considered an ideal system for expressing recombinant proteins due to their similarity to human cells for post-translational protein modification. In addition, CHO cells have a well-characterized approval history for production of clinical grade materials such as recombinant antibody therapeutics.

By creating and evaluating CAT-S and CHO-S cells transfected with the same recombinant IgG construct it has been demonstrated that higher levels of protein expression are achieved in CAT-S cells compared to a known CHO-S host.

The invention claimed is:

1. A Chinese hamster ovary cell line as deposited with the European Collection of Cell Cultures (ECACC) under accession number 10090201 comprising nucleic acid encoding a recombinant polypeptide selected from a therapeutic protein, a recombinant immunoglobulin, and a recombinant fragment thereof.

2. The Chinese hamster ovary cell line of claim 1, wherein the cell line comprises nucleic acid encoding at least two recombinant polypeptides.

3. A kit comprising the Chinese hamster ovary cell line of claim 1 and a vector encoding a recombinant polypeptide.

4. A process for using the Chinese hamster ovary cell line of claim 1 for the production of a recombinant polypeptide, comprising culturing the Chinese hamster ovary cell line of claim 1 to produce the recombinant polypeptide.

5. A method for the production of a recombinant polypeptide comprising culturing the Chinese hamster ovary cell line of claim 1 under appropriate conditions, thereby producing the recombinant polypeptide.

6. A method for the production of a recombinant polypeptide comprising: culturing the Chinese hamster ovary cell line of claim 1 to express the recombinant polypeptide therefrom; and purifying the recombinant polypeptide.

* * * * *